(12) United States Patent
Xia et al.

(10) Patent No.: US 7,489,835 B1
(45) Date of Patent: Feb. 10, 2009

(54) SENSING SYSTEM WITH FIBER GAS SENSOR

(75) Inventors: Hua Xia, Altamont, NY (US); Jeffrey Scott Goldmeer, Latham, NY (US); Kevin Thomas McCarthy, Troy, NY (US); Aditya Kumar, Schenectady, NY (US); Ravindra Annigeri, Roswell, GA (US); Ertan Yilmaz, Albany, NY (US); Avinash Vinayak Taware, Rexford, NY (US); Yu Zhao, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/057,446

(22) Filed: Mar. 28, 2008

(51) Int. Cl.
*G02B 6/00* (2006.01)
(52) U.S. Cl. .......................................... 385/12
(58) Field of Classification Search ............ 385/12, 385/13
See application file for complete search history.

(56) References Cited

U.S. PATENT DOCUMENTS

| | | | |
|---|---|---|---|
| 5,708,735 A | 1/1998 | Benson et al. | |
| 5,783,152 A | 7/1998 | Nave | |
| 6,535,658 B1 * | 3/2003 | Mendoza et al. | 385/12 |
| 7,151,872 B1 | 12/2006 | Xia et al. | |
| 2005/0169807 A1 | 8/2005 | Carpenter et al. | |
| 2006/0215959 A1 | 9/2006 | McCarthy et al. | |

\* cited by examiner

*Primary Examiner*—Charlie Peng
(74) *Attorney, Agent, or Firm*—Ann M. Agosti (57) ABSTRACT

A fiber gas sensor includes a fiber core with first and second refractive index periodic modulated grating structures having different amplitude modulation profiles positioned about the fiber core. A fiber cladding is positioned about the first and second refractive index periodic modulated grating structures. A sensing layer is positioned about the fiber cladding of one of the refractive index periodic modulated grating structures. The sensing layer includes a sensing material made of a Pd-based alloy, such as nano-PdOx, nano-Pd(x)Au(y)Ni(1-x-y) or nano-Pd/Au/WOx. The fiber gas sensor provides a measurement of localized, temperature-corrected gas concentration and composition from a combustion environment. A reflection-based or a transmission-based sensing system with an array of one or more fiber gas sensors is also described.

20 Claims, 8 Drawing Sheets

SENSING SYSTEM WITH FIBER GAS SENSOR

BACKGROUND OF THE INVENTION

This invention relates generally to sensing systems and sensors, and, more particularly, to a sensing system with an array of grating-based fiber gas sensors that provide a measurement of a temperature-corrected gas concentration.

Power generating systems are being built today that have turbines using Syngas (hydrogen ($H_2$) mixing with carbon monoxide (CO)) as fuel. The Syngas can be generated using a coal gasifier or other industrial processes. Also, gas turbines today can use a blend of Natural Gas (NG) and $H_2$ fuel for power generation in order to obtain better operability, efficiency or emissions control. Typically, fuel streams used by turbines could contain Natural Gas (NG), which is primarily methane ($CH_4$), diluents such as nitrogen ($N_2$) and Carbon Monoxide (CO) and Carbon Dioxide ($CO_2$), as well as higher molecular weight hydrocarbons, such as ethane ($C_2H_6$) and propane ($C_3H_8$). A hydrogen containing fuel could be a blend of low percentage of $H_2$ in natural gas, or high percentages of $H_2$ mixed with NG and/or other diluents, or a Syngas mixture, which is $H_2$ with CO. For such applications, it becomes essential to monitor the composition of fuel that is being combusted so that its impact on output and efficiency of the turbines can be effectively controlled. Particularly, when $H_2$-rich Syngas or NG blended with $H_2$ is used as fuel for gas turbine, the fuel composition needs to be monitored online so that it can be controlled for required combustion performance driven by output, emission and efficiency requirement.

Existent $H_2$ sensing technologies are largely unsuitable for direct online $H_2$ concentration or composition monitoring due to several reasons. One reason is that, because of high concentration of $H_2$, such conventional combustible gas sensors get saturated. Only spectroscope-based instruments, such as chromatography, mass spectrometer, Raman spectroscope, ring-down spectrometer, and the like, may be used for offline and not online $H_2$ concentration or composition measurement. At the same time, the difficulty of deploying such bulky and dedicated spectrometry based sensors is obvious, especially, in harsh environments of coal gasifier and Syngas or natural gas combustors for real-time online monitoring/analysis of fuel quality. Although there are several conventional combustible gas sensors, such as infrared, electrochemical, metal oxide semiconductor based combustible gas-detection devices, they are either insensitive to hydrogen gas or saturated by high concentration or cannot be deployed in the harsh environments.

Other optical methods, such as fiber optic evanescent field-based, near infrared laser absorption, have been developed for $H_2$-rich Syngas analysis. Usually, these gas-sensing devices require transparent medium and thermal sensitive optical parts installation. Thus, there is a need to provide a practical solution for online Syngas analysis for power generation performance in an environment such as gas turbine, combustor, and gasifier etc, as well as power generation efficiency control and optimization.

BRIEF DESCRIPTION OF THE INVENTION

In one aspect, a fiber gas sensor comprises a fiber core having a longitudinal axis; a first refractive index periodic modulated grating structure having a first amplitude modulation profile positioned about the fiber core for sensing a localized gas concentration; a second refractive index periodic modulated grating structure having a second amplitude modulation profile positioned about the fiber core at a distance along the longitudinal axis with respect to the first refractive index periodic modulated grating structure for sensing a localized temperature; a fiber cladding positioned about the first and second refractive index periodic modulated grating structures; and a sensing layer positioned about the fiber cladding of the first refractive index periodic modulated grating structure, the sensing layer including a sensing material made of a group consisting of nano-PdOx, nano-Pd(x)Au(y)Ni(1-x-y) and nano-Pd/Au/WOx, wherein the gas sensor is capable of providing a temperature-corrected determination of the localized gas concentration.

In another aspect, a fiber gas sensor comprises a fiber core having a longitudinal axis; a long-period fiber grating structure having a first amplitude modulation profile positioned about the fiber core for sensing a localized gas concentration; a short-period fiber grating structure having a second amplitude modulation profile positioned about the fiber core at a distance along the longitudinal axis with respect to the long-period fiber grating structure for sensing a localized temperature; a fiber cladding positioned about the long-period and short-period fiber grating structures; and a sensing layer positioned about the fiber cladding of the long-period fiber grating structure, the sensing layer including a sensing material made of a group consisting of nano-PdOx, nano-Pd(x)Au(y)Ni(1-x-y) and nano-Pd/Au/WOx, wherein the gas sensor is capable of providing a temperature-corrected determination of the localized gas concentration.

In yet another aspect, a sensing system comprises at least one fiber gas sensor; a FC/APC connector operably coupled to each fiber gas sensor; and one of an optical splitter/combiner and an optical switch operably coupled to the FC/APC connector.

DETAILED DESCRIPTION OF THE INVENTION

Figure 1:
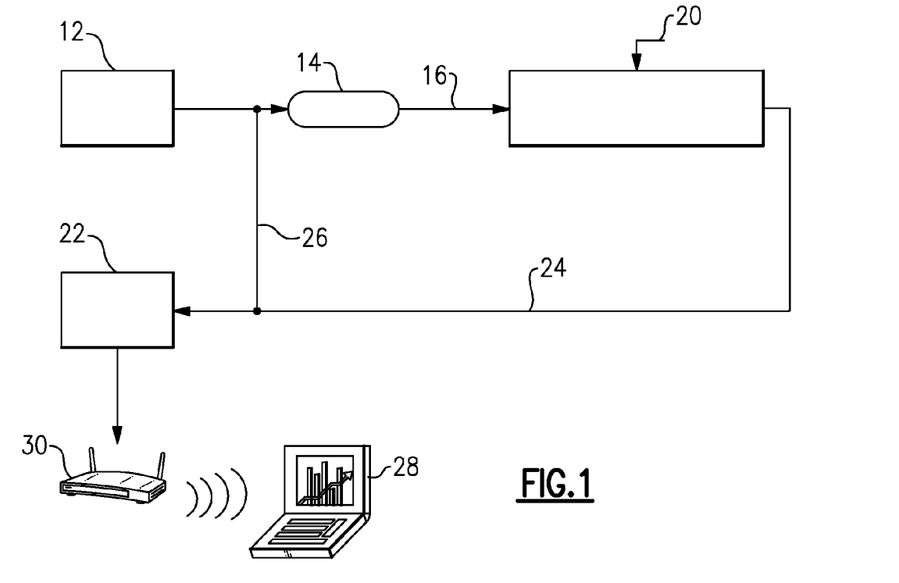
FIG. 1 is a schematic view of a sensing system including a fiber gas sensor (FGS) of the invention for monitoring the operating conditions and/or parameters of a power generating system.

Referring now to FIG. 1, a sensing system 10 is schematically shown according to an embodiment of the invention. In general, the sensing system 10 includes a light source 12, such as tunable, broadband light source, in light communication with an optical coupler or circulator 14. The optical coupler 14 receives the light transmitted from the light source 12 and transmits a portion of the light through an optical fiber cable 16. The light passing through the optical fiber cable 16 enters one or more fiber gas sensors (FGS), shown generally at 20, according to the invention. A photodetector 22 positioned downstream of the fiber gas sensor 20 receives the transmitted light from the gas sensor 20 through an optical fiber cable 24. A portion of the light reflected by the optical coupler 14 is also received by the photodetector 22 through an optical fiber cable 26. The light signal generated by fiber gas sensor(s) 20 is processed and/or transmitted to a computer 28. In an embodiment, a wireless interface 30 transmits electrical signals to the computer 28 generated by the photodetector 22 in response to light signals received from the one or more fiber gas sensor(s) 20.

The FGS 20 monitors the operating conditions and/or parameters of a power generating apparatus (not shown), such as a gas turbine, combustor, a coal gasifier, and the like. Such operating conditions and/or parameters include, but are not limited to, internal temperatures, pressures, and/or the presence and concentration levels of combustion gases generated within the apparatus. A control system (not shown), such as a gas turbine control system, is in operating control communication with gas sensor(s) 20 to receive signals generated as a result of sensor detection and to control the operation of the apparatus to reduce emissions and increase power generation efficiency by controlling burner fuel to air ratios and/or total airflow to the turbine system. In one embodiment, efficiency is optimized by reducing fouling and/or slag, for example by using the sensed temperatures, strains or pressures to detect a level of slag and/or fouling. In another embodiment, efficiency is optimized by maintaining a right ratio of fuel to air, for example by using the sensed hydrogen gas concentration or natural gas concentration to control combustion process.

Figure 2:
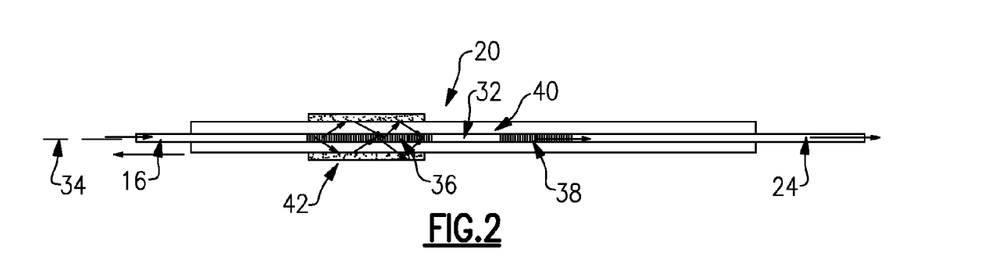
FIG. 2 is a schematic view of the fiber gas sensor shown in FIG. 1.

Referring now to FIG. 2, the fiber gas sensor 20 is shown according to an embodiment of the invention. In general, the fiber gas sensor 20 includes a central fiber core 32 formed of GeO$_2$ and F co-doped silica that extends along a longitudinal axis 34 and having a diameter of about 5 microns to about 9 microns. The fiber core 32 includes two refractive index periodic modulated gratings having different amplitude modulation profiles, either apodized or blazed or their combination, for increasing guided core mode coupling to cladding modes.

In one embodiment, one of the refractive index periodic gratings comprises a long-period fiber grating (LPG) structure 36 positioned about the fiber core 32 and the other grating comprises a short-period fiber grating structure 38 positioned about the fiber core 32 at a distance along the longitudinal axis 34 with respect to the long-period fiber grating structure 36. In a particular embodiment, the short-period fiber grating structure 38 comprises a fiber Bragg grating (FBG) structure 38 that has highly thermal stability performance.

A fiber cladding 40 is circumferentially disposed about the fiber core 32 and has an outer diameter of about 125 microns made from pure silica. In one embodiment, the fiber cladding 40 is configured to act as a waveguide for light propagation through the fiber core 32. The broadband tunable light source 12 is positioned in light communication with the optical fiber cable 16 and emits a near infrared light that propagates through the fiber core 32.

In a particular embodiment, the FGS 20 has a length along the longitudinal axis 34 of the optical fiber core 32 of about 10 millimeters to about 50 millimeters. The LPG structure 36 has a length along the longitudinal axis 34 of about 10 millimeters to about 30 millimeters with a cladding diameter of about 0.05 millimeter to about 0.125 millimeters. The LPG structure 36 has a modulation along the longitudinal axis 34 with a pitch size of about 100 microns to about 600 microns. The LPG structure 36 is configured to effectively shed fundamental mode energy to the modes of the fiber cladding 40. When the refractive index of the sensing material of the sensing layer 42 is lower than the fiber cladding 40, the modes of the fiber cladding 40 are guided by sensing material/cladding and fiber core interfaces. Partial light energy dissipates into the sensing material by evanescent field; to the contrary, the cladding modes partially dissipate the energy into the sensing coating layer as radiation modes. The FBG structure 38 has a length along the longitudinal axis 34 of about 3 millimeters to about 10 millimeters with a cladding diameter of about 0.125 millimeters. As a general rule, the length of the LPG structure 36 is about 2 to 5 times the length of the FBG structure 38 that enables the transmission spectrum of the LPG structure 36 to have a narrow line width of less than 12 nm and a higher dynamic range of greater than 10 dB.

A fiber gas sensing layer 42 is disposed about the fiber cladding 40 of the long-period fiber grating (LPG) structure 36. In the illustrated embodiment, the gas sensing layer 42 is only disposed about the LPG structure 36 and not the FBG structure 38. However, the invention can be practiced with the sensing layer 42 disposed about the FBG structure 38. The sensing layer 42 is configured to effectively assist the coupling of the mode of the fiber cladding 40 to the fundamental mode by a refractive index variation, an optical absorption change, or a sensing material stress change. Thus, the light signal that is reflected and/or redirected by the FGS 20 to the photodetector 24 depends upon the measurands and operation.

The sensing layer 42 includes a sensing or chemical gas active material including at least one base material, such as (Pd, Pt)-doped WOx, PdOx, and ternary Pd(x)Au(y)Ni(1-x-y) alloy. The morphology of the sensing material may comprise nanoparticles having a diameter of about 5 nm to about 10 nm. In one embodiment, the sensing layer 42 includes a sensing material with chemical gas sensitivity, which is sensitive and/or activated by interactions with a chemical gas that induces a refractive index variation, an absorption change, or a sensing material stress change.

In one embodiment, sensing layer 42 includes a sensing material that is sensitive to the presence of $H_2$ and/or $H_2$+Natural gas (NG). For example, sensing layer 42 includes a Palladium based alloy, such as, but not limited to, nano-(Pd, Pt)-WOx (x=2.7-3.0) sensing material, PdOx, and/or a nano-Pd(x)Au(y)Ni(1-x-y) ternary sensing material. In this embodiment, adsorbed H atoms interact with palladium to form hydride. The hydrides in the sensing material result in a strong structural phase transition from alpha phase to beta phase or their mixed intermediate phase, thereby varying the refractive index of the coated sensing material, and altering the light coupling between the fundamental mode and cladding mode, and the coupling between the cladding mode and radiation mode in both the long-period grating cladding 40 and the sensing layer 42. This enables an observable change in both transmission and reflection, and eventually leads to the identification of the $H_2$ gas adsorbed. Simultaneous mapping of $H_2$ gas concentration and localized temperature value is obtained with the same gas sensor 20 using the multifunctional and differential interrogation configuration of the present invention.

The palladium-based alloy sensing material is opaque and becomes semi-transparent when it interacts with hydrogen to form a hydride. Actually, the alpha-phase of hydride will transform to beta-phase, accompanying a change in dielectric function, or refractive index. Using this phase transition property, the fiber $H_2$ sensor can detect such a dielectric function difference. The formation of the hydride actually changes the cladding mode boundary and coupling efficiency so that the transmission wavelength and its power loss of the fiber grating-based hydrogen sensor are modulated.

For environmental temperatures of less than about 1000° F., the sensing layer 42 may include a base material of $WO_3$ or $SiO_2$. The $SiO_2$ base material is doped with suitable material nanoparticles of Pd, Pt, Au, Ag and/or Ni. The nanoparticles have a diameter of about 5 nm to about 10 nm. In this embodiment, the sensing layer 42 is prepared using a sputtering process or thermal evaporation process. It is apparent to those skilled in the art and guided by the teachings herein provided that any suitable process can be used to prepare the sensing layer 42. After the sensing layer 42 is prepared, the sensing layer 42 is annealed in an $Ar^+$ environment for about 2 hours at about 600° C. or until the sensing material has a nanoparticle size of less than about 10 nm.

In one embodiment, the sensing layer 42 includes a gas active nanoparticle material. In this embodiment, the sensing layer 42 has a thickness that allows a few cladding modes propagation when a refractive index of sensing layer 42 is close to the refractive index of fiber cladding 40. Alternatively, sensing layer 42 has a thickness that allows a few radiation modes propagation when a refractive index of sensing layer 42 is greater than a refractive index of fiber cladding 40. Further, sensing layer 42 has a thermal expansion coefficient different from a thermal expansion coefficient of fiber cladding 40 such that a material induced interfacial strain is needed to be controlled by choosing sensing coating layer thickness lower than 100 nm. In a particular embodiment of gas sensing at an elevated temperature, the interfacial strain between sensing layer 42 and fiber cladding 40 is thermally compensated for by a nanoporous sensing material morphology so that sensing material thermal effect is dominated by fiber cladding. In an alternative embodiment, optical fiber cable 16 is hermetical sealed either with a hydrophobic membrane (PTFE for T<200° C.) (not shown) or a porous ceramic ($Al_2O_3$ for T>200° C.) thin layer to protect the sensing gas sensor 20 and allow only gas penetration.

In another embodiment, the sensing layer 42 includes an integration of Pd-based alloys, such as, but not limited to, nano-PdOx or Pd(x)Au(y)Ni(1-x-y) sensing materials, for environmental temperatures less than about 400° C., and nano-Pd/Au/WOx sensing material for environmental temperatures at least about 400° C. The sensing layer 42 includes a circumferentially coated thin film that functions as a $H_2$ and $CH_4$ blended $H_2$ gas sensor. The hydride formation result in a strong sensing material nanostructural change, which varies the refractive index of the coated sensing material, and alters the light coupling between the fundamental mode and cladding modes, and the coupling between the cladding modes and radiation modes in the long-period grating-cladding area and in the sensing layer 42.

Figure 3:
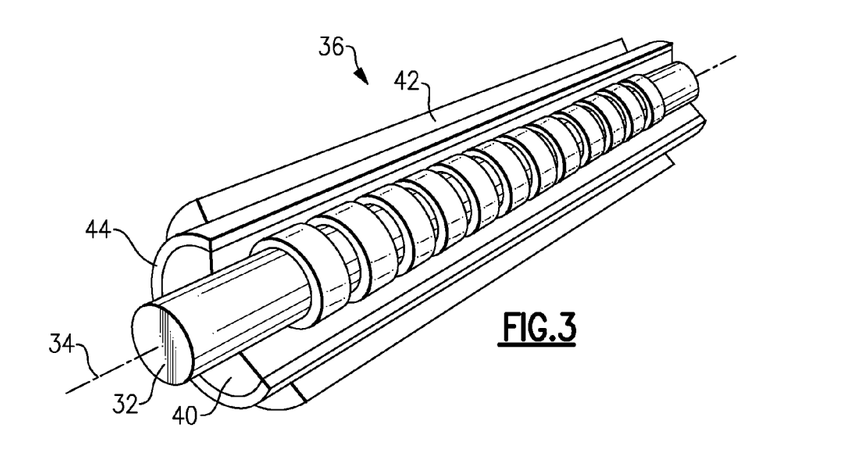
FIG. 3 is a partial cross-sectional view of a long-period grating (LPG) structure of the gas sensor shown in FIG. 2.

Referring now to FIG. 3, an adhesive layer 44 may be applied to the fiber cladding 40 to enhance the bonding between the fiber cladding 40 and the sensing layer 42. In an embodiment, the adhesive layer 54 may comprise a layer of nickel having a thickness of about 5 nm. In another embodiment, the adhesive layer 54 may comprise a layer of titanium having a thickness of about 5 nm. Before depositing the adhesive layer 44, the surface of the fiber cladding 40 may be treated with 50% HF for 5 minutes and followed with a de-ion water resin and $N_2$ dry process.

In operation, as the light is first transmitted through the FGS 20, the selected wavelength of light from the light source 12 enters the LPG structure 36 and undergoes a wavelength shift and a loss in transmission power in the form of discrete wavelength peaks that corresponds to at least one operating condition and/or parameter, such as a concentration of $H_2$, $H_2$+Natural gas (NG) or the concentration of other combustible gases. As the light continues through the FGS 20, the light enters the FBG structure 38 and undergoes a wavelength shift that corresponds to at least one operating condition and/or parameter, such as temperature, and the like.

In operation, the sensing system 10 can be kept at a constant temperature condition that corresponds to an optimized $H_2$ sensitivity and selectivity, provided by a thermal heating element surround the sensor package. In another aspect, the sensing system can be operated at a modulated temperature condition that is used to distinguish different compositions and $H_2$ blended gases by the temperature sensitivity of the gas composition.

The sensing system 10 can operate in two modes of operation: 1) a reflection-based sensing system, or 2) a transmission-based sensing system. In either sensing system 10, the gas sensor 20 of the invention provides a determination of a temperature-corrected gas concentration. In the transmission-based sensing system, the light passing once through the both the LPG structure 36 and the FBG structure 38 of the gas sensor 20 enters the fiber cable 24 and is received by the photodetector 22. The LPG structure 36 causes a transmission power loss in the light signal due to the sensitivity of the sensing layer 42 to a gas, such as $H_2$, $H_2$+$N_2$, and the like. Further, the wavelength shift from the LPG structure 36 and the FBG structure 38 can be used to determine environmental temperature. The transmission power loss from the LPG structure 36 and the difference in temperature from the LPG structure 36 and the FBG structure 38 can be used to determine a temperature-correction gas concentration.

In the reflection-based sensing system 10, the light that passes through the LPG structure 36 is reflected back by the FBG structure 38 and passes again through the LPG structure 36. The reflected light enters the optical coupler 14, transmitted through the fiber cable 26 and is received by the photodetector 22. The LPG structure 36 causes a transmission power loss in the light signal due to the sensitivity of the sensing layer 42 to a gas, such as $H_2$, $H_2+N_2$, and the like. The wavelength shift from the FBG structure 38 can be used to determine environmental temperature. The difference in the transmission power loss from the light passing twice through the LPG structure 36 and the temperature from the FBG structure 38 can be used to determine a temperature-corrected gas concentration.

Such a modulation in both wavelength shift and power loss proportional to gas concentration, such as $H_2$ concentration, provides a "digital" $H_2$ concentration measurement in terms of wavelength shift and an "analog" $H_2$ concentration measurement in terms of resultant transmission power loss. These two sensor responses provide inherently integrated hydrogen sensing method.

Because the FBG structure 38 is located in approximately the same environment as the LPG structure 36, the relative wavelength shift of the FBG structure 38 can be used to determine the environmental temperature in real-time, and the change in reflected transmission power loss can also be used for the determination of gas concentration since the light twice passes the sensing grating. Moreover, the wavelength shift and transmission power loss of the LPG structure 36 can be used for the real-time determination of gas concentration and composition under either constant temperature or modulated temperature operation conditions. This simultaneous detection of localized temperature, gas concentration and composition has improved sensor performance and reduced low false positive rate, thereby providing an accurate measurement of the $H_2$ gas concentration, regardless of temperature variations and/or other spurious events.

Referring back to FIG. 2, the long-period fiber grating structure 36 and the short-period fiber grating structure 38 have a profile that is substantially parallel and uniform spacing with respect to the longitudinal axis 34 of the fiber cable. However, the invention can be practiced with other types of long-period and short-period fiber grating structure profiles. For example, the long-period fiber grating structure 36 and/or the short-period fiber grating structure 38 may comprise a fiber grating structure having a blazed grating profile with an angle of about 1 degree to about 40 degree with respect to the longitudinal axis 34 of the fiber cable. In another example, the long-period fiber grating structure 36 and/or the short-period fiber grating structure 38 may comprise a non-uniform grating profile, such as an apodized fiber grating structure that may have, for example, a Gaussian shape, a cosine shape, and the like. In yet another example, the non-uniform grating profile may be a combination of a blazed and an apodized grating profile. All four types of gratings (uniform, blazed, apodized, blazed and apodized) have a typical length of about 10 millimeters to about 30 millimeters, and a cladding diameter of about 0.05 millimeters to about 0.125 millimeters.

Because the fiber gas sensor 20 can be any combination of four types of grating profiles (uniform, blazed, apodized, and blazed and apodized), there are several types of FBS 20. For example, a first type of FGS 20 has a uniform grating profile for the LPG structure 36 and the FBG structure 38. A second type of FGS 20 has a blazed grating profile for the LPG structure 36 and the FBG structure 38. A third type of FGS 20 has an apodized grating profile for the LPG structure 36 and the FBG structure 38. A fourth type of FGS 20 has a blazed and apodized grating profile for the LPG structure 36 and the FBG structure 38. A fifth type of FGS 20 has a uniform grating profile for the LPG structure 36 and an apodized grating profile for the FBG structure 38. A sixth type of FGS 20 has a blazed grating profile for the LPG structure 36 and an apodized grating profile for the FBG structure 36. It will be appreciated that other combinations of grating profiles for the LPG structure 36 and the FBG structure 38 are within the scope of the invention.

In the illustrated embodiment, the FGS 20 comprises a long-period fiber grating structure 36 coated with the gas sensing layer 42 and a short-period fiber grating structure 38 without the gas sensing layer 42. In an alternate embodiment, the FGS 20 may comprise a pair of a short-period fiber grating (FBG) structures 38 with one of the FBG structures 38 having the gas sensing layer 42 and the other FBG structure 38 without the gas sensing layer 42. Because both fiber grating structures 36, 38 are sensitive to temperature, a differential determination of the gas concentration and composition is done by referencing the temperature determining of the second FBG structure 38. Similar to the LPG structure 36 and the FBG structure 38 in the illustrated embodiment discussed above, the alternate embodiment of the FGS 20 with the pair of FBG structures 38 can be any combination of grating profiles (uniform, blazed, apodized, blazed and apodized). That is, a first type of FBS 20 has a uniform grating profile for both the FBG structures 38. A second type of the FGS 20 has a blazed grating profile for both the FBG structures 38. A third type of the FBS 20 has an apodized grating profile for both the FBG structures 38. A fourth type of the FBS 20 has a blazed and an apodized grating profile for both the FBG structures 38. A fifth type of the FGS 20 has a uniform grating profile for one FBG structure 38 and an apodized grating profile for the other FBG structure 38. A sixth type of the FBS 20 has a blazed grating profile for one FBG structure 38 and an apodized grating profile for the other FBG structure 38. It will be appreciated that other combinations of grating profiles for the FBG structures 38 are within the scope of the invention.

Figure 4:
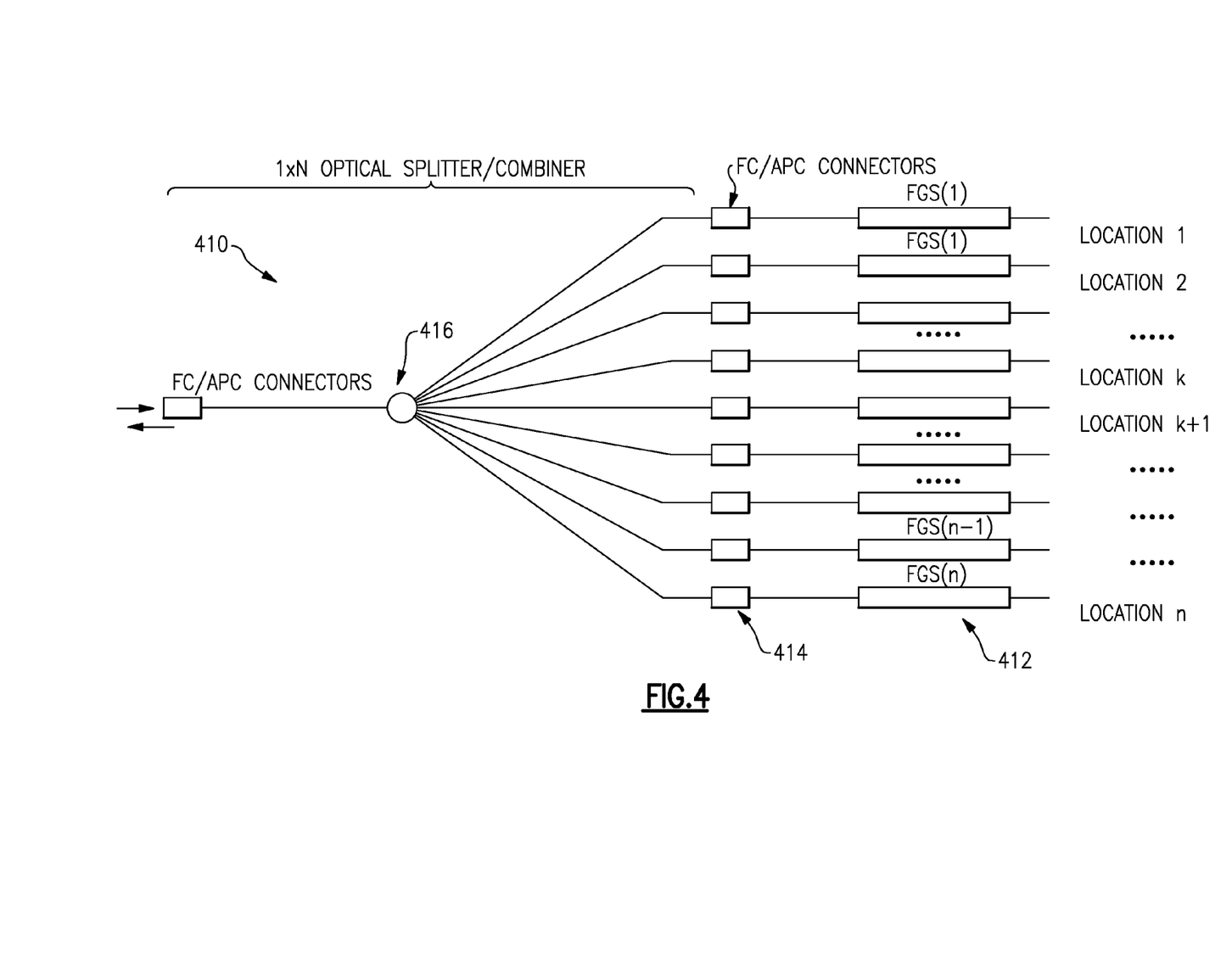
FIG. 4 is a schematic view of distribution method of the fiber gas sensor (FGS) for multi-point gas sensing in a reflection-based gas sensing system.

Referring now to FIG. 4, a reflection-based sensing system 410 in which an array 412 one or more fiber gas sensors 20 are distributed in an industrial environment, such as a boiler, combustor, gasifier, and engine, and the like, is schematically shown. In the reflection-based sensing system 410, for example, the combustible gas can be measured from the reflection at n locations. Each fiber gas sensor (FGS) 20 is connected to the sensing system 410 by a fiber connector/angled polish connector (FC/APC) connector 414 and a 1×n optical splitter/combiner 416. In one embodiment, the optical splitter/combiner 416 is of 1×2, 1×3, 1×4, and 1×8 types. In another embodiment, an optical switch of 1×16 is used to replace the optical splitter/combiner 416 for multi-point combustible gas sensing. The reflected light signal from each fiber gas sensor 20 is characterized by their wavelength shift for temperature calibration, and by their reflected power loss response for gas concentration monitoring.

Figure 5:
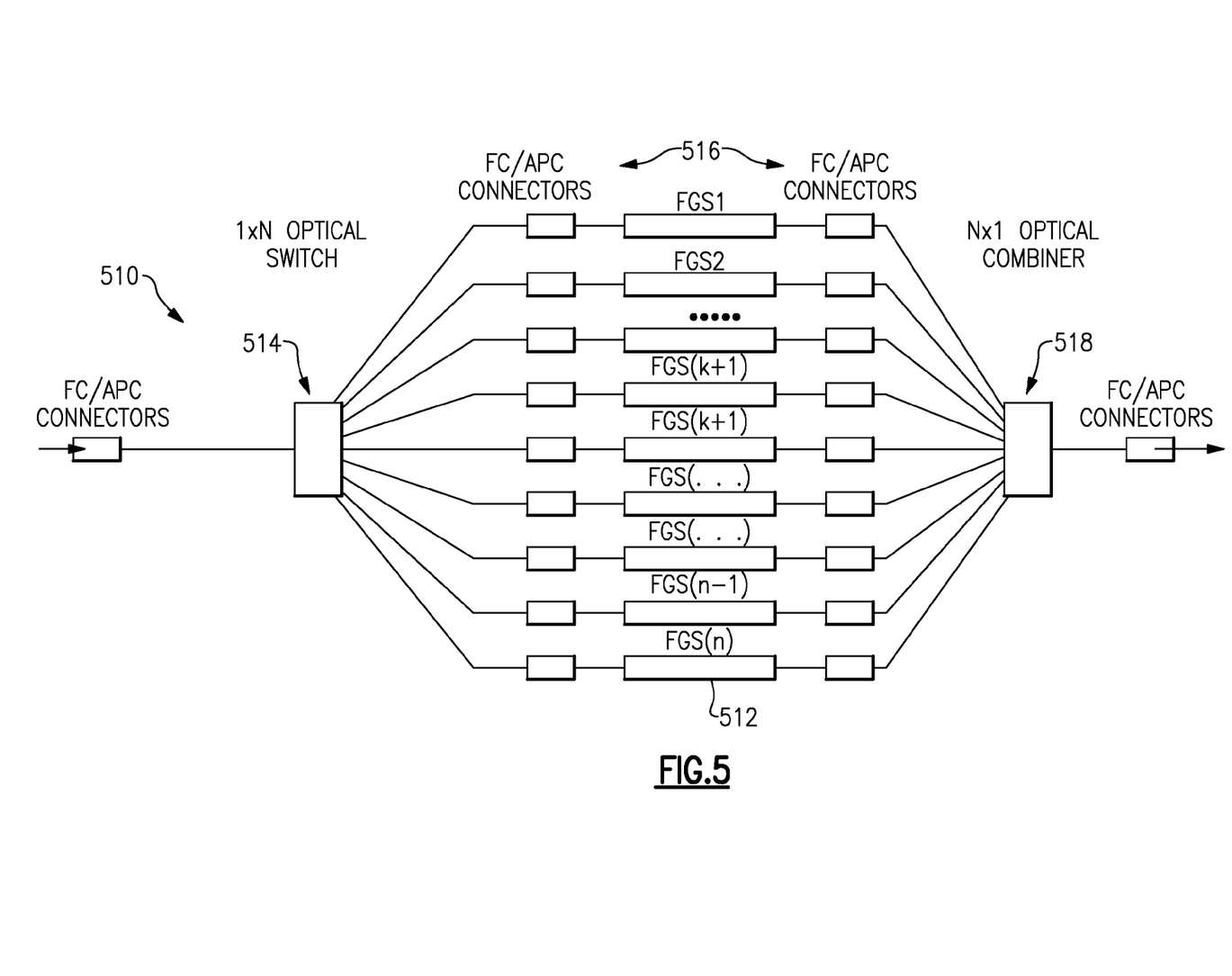
FIG. 5 is a schematic view of distribution method of the fiber gas sensor (FGS) for multi-point gas sensing in a transmission-based gas sensing system.

Referring now to FIG. 5, a transmission-based sensing system 510 in which an array 512 one or more fiber gas sensors 20 are distributed in an industrial environment, such as a boiler, combustor, gasifier, and engine, and the like, is schematically shown. In the transmission-based sensing system 510, for example, the combustible gas can be measured from the reflection at n locations. Each fiber gas sensor (FGS) 20 is connected to the sensing system 510 by a 1×n optical switch 514. Each fiber gas sensor (FGS) 20 is connected to the sensing system 510 by a FC/APC connector 516 and n×1 optical combiner 518. In one embodiment, the optical switch 514 and the optical combiner 518 is of 1×2, 1×3, 1×4, and 1×8 types. In another embodiment, an optical combiner and switch of 1×16 is used for multi-point combustible gas sensing. The transmitted signal from each fiber gas sensor 20 is characterized by their wavelength shift and transmitted power loss response for gas concentration monitoring in which the wavelength shift of the short-period Bragg grating is used for environmental temperature calibration.

It will be appreciated to those skilled in the art and guided by the teachings herein provided that in alternative embodiments, any suitable number of fiber optic hydrogen sensing devices can be used in applications that need hydrogen sensing, such as a power generating system turbines using hydrogen for combustion. The flexibility of having multiple gas sensing elements on the same fiber allows for multiple point combustible gas measurement at higher spatial resolution. Multiple such sensors can be either cascaded or in parallel for multi-point on one gas concentration detection. Thus, multiple measurands capability with higher spatial resolution is one of the biggest merits of the fiber optic grating based sensing system. The other merit is that different fiber gas sensors can be cascaded in one sensing system for multi-composition ($H_2$, CO, $CH_4$, etc) online monitoring.

Figure 6:
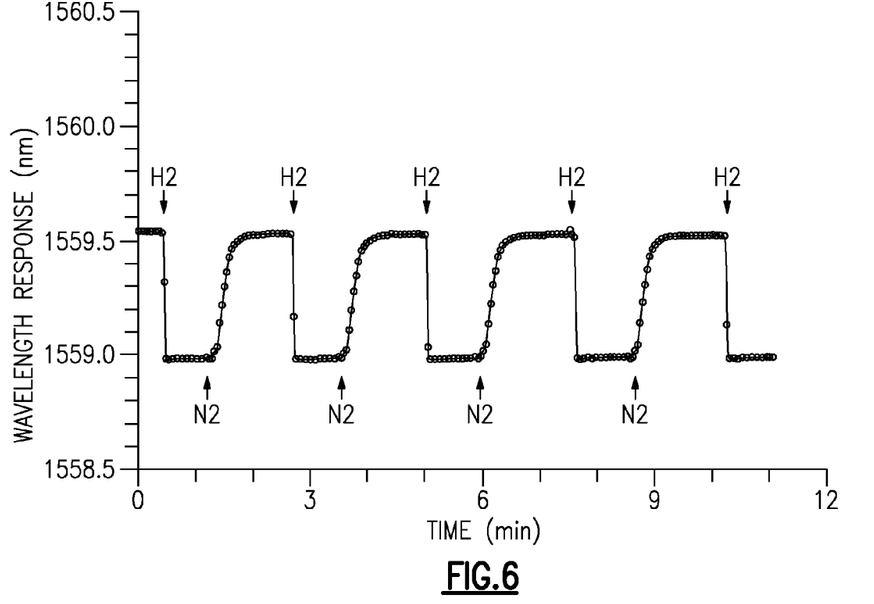
FIG. 6 is a graphical representation of time versus wavelength for a signal transmitted through the fiber gas sensor of the invention for 75% $H_2$ concentration mixed with $N_2$ at 131 deg. F.
Figure 7:
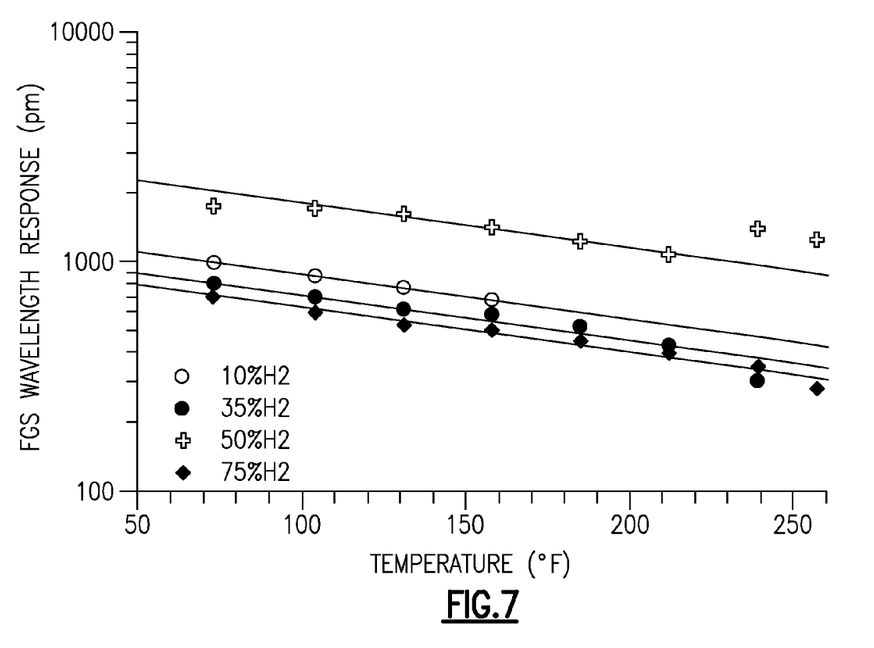
FIG. 7 is a graphical representation of wavelength shift at different hydrogen concentrations at elevated temperature from the fiber gas sensor of the invention.
Figure 8:
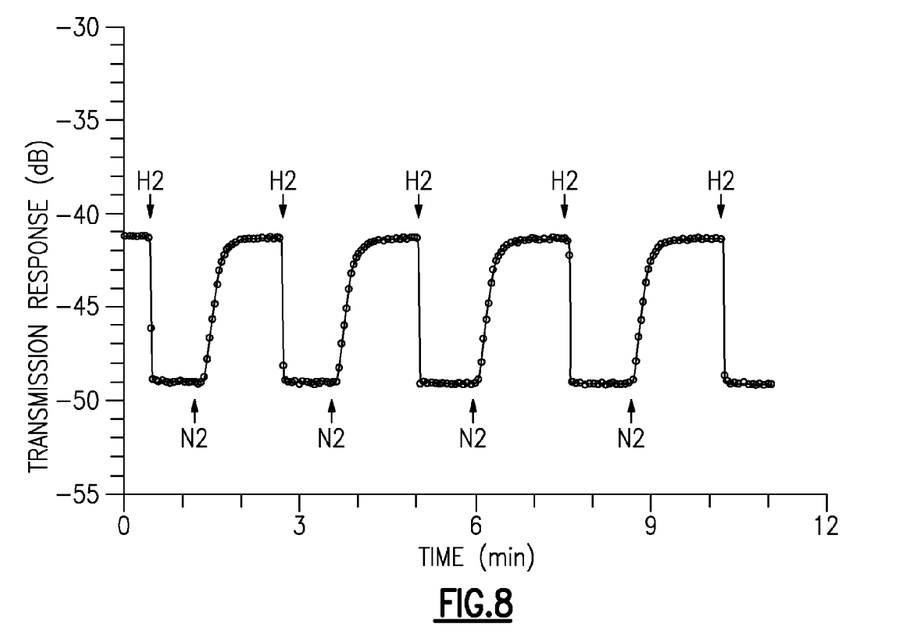
FIG. 8 is a graphical representation of transmission power loss versus time for a signal transmitted through the fiber gas sensor of the invention for 75% $H_2$ concentration mixed with $N_2$ at 131 deg. F.

Feasibility studies so far have demonstrated that the current prototype fiber optic hydrogen-sensing device could be used in a harsh environment. FIGS. 6 and 7 show the wavelength shift ($\Delta\lambda$) response from the fiber gas sensor 20 of about 0.01 nm to about 2.0 nm for hydrogen gas concentration from about 10% to about 75% and the environmental temperature from ambient temperature to about 260° F. The sensor response time (time it takes for complete wavelength shift to occur upon introduction of $H_2$) is typically about 3.5 s and recovery time (time for wavelength to return to baseline upon $N_2$ purge) is up to about 25 s. As shown in FIG. 6, the transmission power loss ($\Delta P$) was about 7.8 dB. FIG. 8 shows the transmission power loss ($\Delta P$) from the fiber gas sensor 20 ranging from about 0.2 dB to about 7.8 dB for hydrogen gas concentration from about 10% to about 75% and the environmental temperature from ambient temperature to about 260° F.

Figure 9:
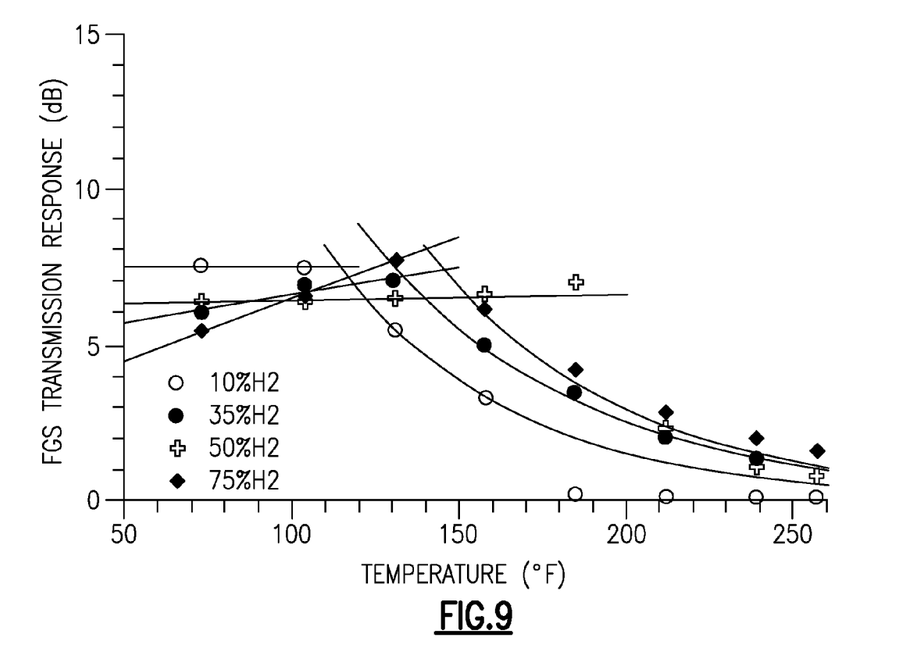
FIG. 9 is a graphical representation of response time of fiber gas sensor of the invention to different hydrogen concentrations at elevated temperature.
Figure 10:
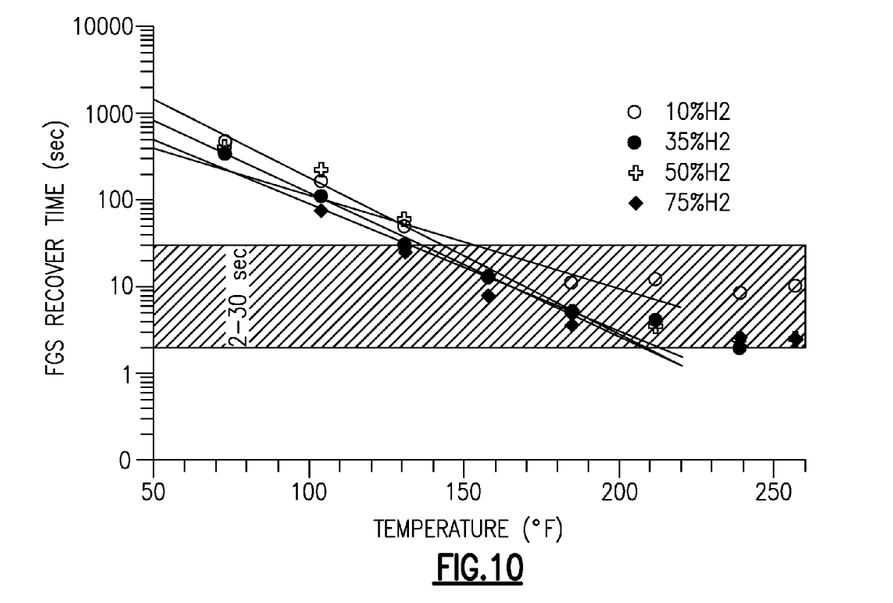
FIG. 10 is a graphical representation of recovery time of fiber gas sensor of the invention to different hydrogen concentrations at elevated temperature.

The transmission response in dB and the recovery time of the fiber gas sensor 20 at different hydrogen concentrations at elevated temperature are shown in FIGS. 9 and 10, respectively. As shown in FIG. 10, the response time and the recovery time ranges from a few hundred seconds to several seconds, depending largely upon the sensing environmental temperature. It should be noted that such a response characteristic of the fiber gas sensor 20 requires a fiber Bragg grating structure 38 to provide an in-line (real-time) temperature measurement for differentiation of the response of the gas sensor 20 to both temperature and gas concentration.

As described above, a $H_2$ sensing device and system is based on fiber grating-based wavelength multiplexing technology with an integration of nanophase sensing material. The long-period grating 30 is inscribed into the optical fiber, with light being shed to cladding at grating location. The fiber cladding 24 is deposited with a nanophase sensing material of 20-30 nm thick. In the absence of any $H_2$ or measurand, the PdOx and PdAuNi based sensing materials look like a metallic mirror that can reflect the cladding modes back into the fiber core. The formation of the hydride in the sensing layer actually changes the cladding mode boundary and coupling efficiency so that the transmission wavelength and its power loss of the fiber grating-based hydrogen sensor are modulated.

Because the sensing material can be tailored by deposition process, it becomes powerful to fabricate different sensing material on the fiber-grating surface for detecting different components of process stream, for instance, for Syngas, it would be, $H_2$ and natural gas blended $H_2$ fuels. The flexibility of having multiple parameter sensitive elements on the same fiber as well multiple elements for such each of these parameters allows for multiple parameter measurement at higher spatial resolution. For example, in the $H_2$ sensing application, sensing elements for temperature are also included to correct the $H_2$ measurements for temperature variation. At the same time, several sensing elements could be mounted on a single fiber allowing for higher spatial resolution of both $H_2$ and temperature. Thus, multiple measurements capability with higher spatial resolution is one of the biggest merits of the fiber optic grating based sensing system.

Several feasibility studies were conducted to determine that the morphology of the sensing material of the sensing layer 42 can be controlled so that the hydrogen gas atoms can be easily diffused into the sensing layer, but not other hydrocarbon gases due to their larger atomic or molecular sizes.

Figure 11:
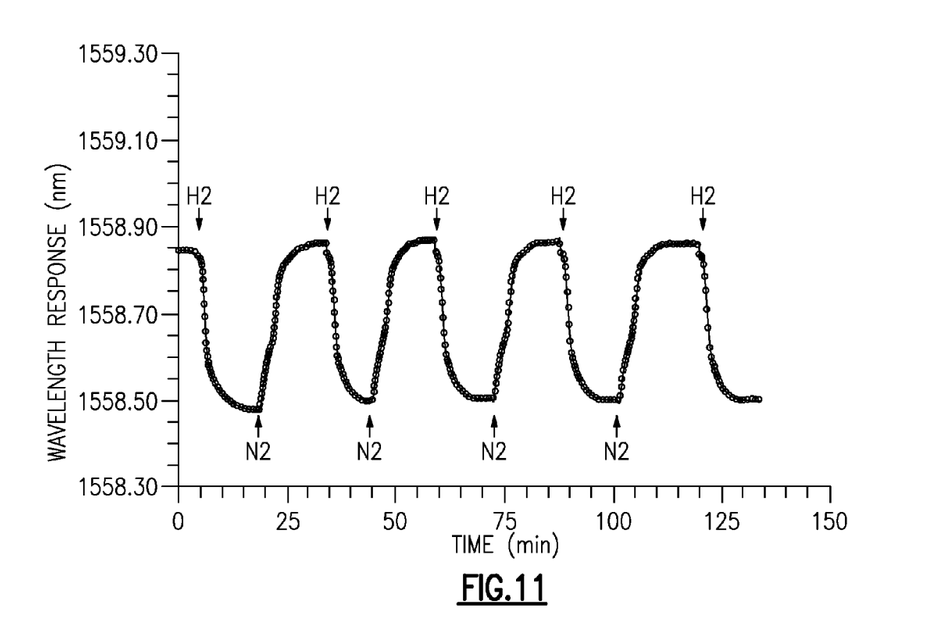
FIG. 11 is a graphical representation of wavelength shift response of the fiber gas sensor of the invention induced by a fuel of about 5% hydrogen blended with CH$_4$ and other hydrocarbon gases at about 104° F.
Figure 12:
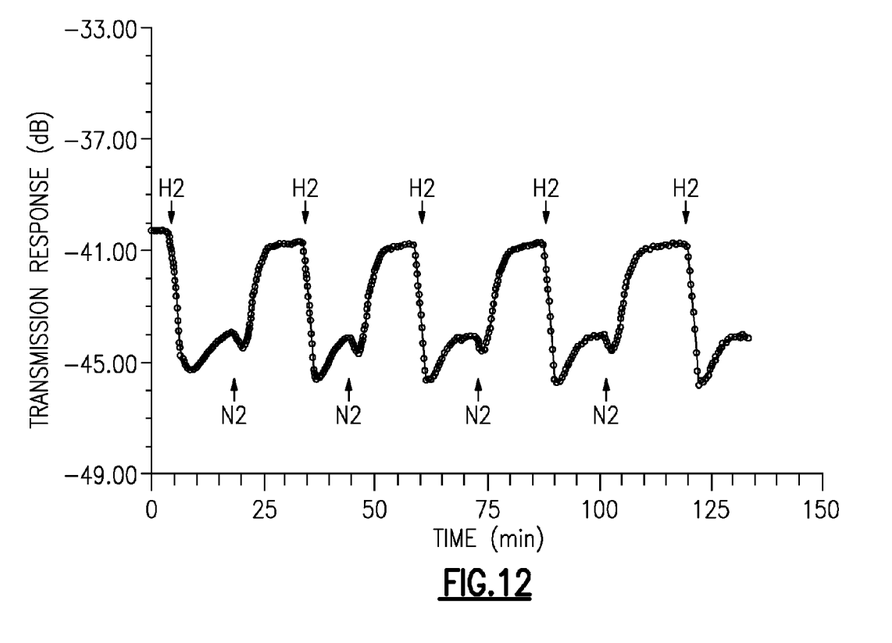
FIG. 12 is a graphical representation of the transmission power loss response of the fiber gas sensor of the invention induced by a fuel of about 5% hydrogen blended with CH$_4$ and other hydrocarbon gases at 104° F.

In one feasibility study, the morphology of the sensing material had a nanoparticle size in a range between about 3 nm to about 5 nm. As shown in FIGS. 11 and 12, the wavelength shift and transmission power loss responses of the gas sensor 20 are significant and repeatable during cycling tests for a fuel used in gas turbine having about 5% $H_2$ blended with about 92% $CH_4$, and other hydrocarbon gases at a temperature of about 104 F. The feasibility study has demonstrated that the sensing layer 42 of the fiber gas sensor 20 of the invention can be configured to detect the presence of $H_2$, and in particular, $H_2$ mixed with Natural gas (NG) that are typically found in the fuel composition of an operating gas turbine (not shown). Table I is a summary of gas turbine fuel composition of about 5% hydrogen blended with about 92.7% $CH_4$, 0.74% $CO_2$, 1.47% $C_2H_6$, 0.13% $C_2H_4$, and other gas compositions. It is apparent to those skilled in the art that sensing layer 42 can be fabricated using a deposition process to sense or detect any desired chemical gas either by sputtering, thermal evaporation, sol-gel dip coating and other thin film deposition processes.

TABLE I

Gas Turbine Fuel Composition

| Specie | % of total = Formula | Typical Nat | Lean Off gas (3 day data) | Typical off gas (3 day data) | Rich off gas (3 day data) | Typical off gas | Mix gas |
|---|---|---|---|---|---|---|---|
| | | 88.36% | 0.00% | 0.00% | 0.00% | 11.64% | 100.00% 0 |
| Hydrogen | H2 | 0.480 | 8.7202 | 20.5043 | 30.954 | 38 | 4.845504 |
| Carbon Dioxide | CO2 | 0.840 | | | | | 0.742265 |
| Methane | CH4 | 96.950 | 91.1785 | 79.44 | 68.9479 | 60.5 | 92.70899 |
| Ethane | C2H6 | 1.610 | 0.000 | 0.0165 | 0.0074 | 0.4 | 1.469215 |
| Propane | C3H8 | 0.090 | | | | | 0.079528 |
| n-Butane | C4H10 | 0.020 | | | | | 0.017673 |

TABLE I-continued

Gas Turbine Fuel Composition

|  |  | Typical Nat | Lean Off gas (3 day data) | Typical off gas (3 day data) | Rich off gas (3 day data) | Typical off gas | Mix gas |
|---|---|---|---|---|---|---|---|
| n-Pentane | C5H12 | 0.010 |  |  |  |  | 0.008836 |
| Ethene (Ethylene) | C2H4 |  | 0.082 | 0.0658 | 0.0907 | 1.1 | 0.127987 |
|  |  | 100.00 | 99.98 | 100.03 | 100.00 | 100.00 | 100.00 |

Figure 13:
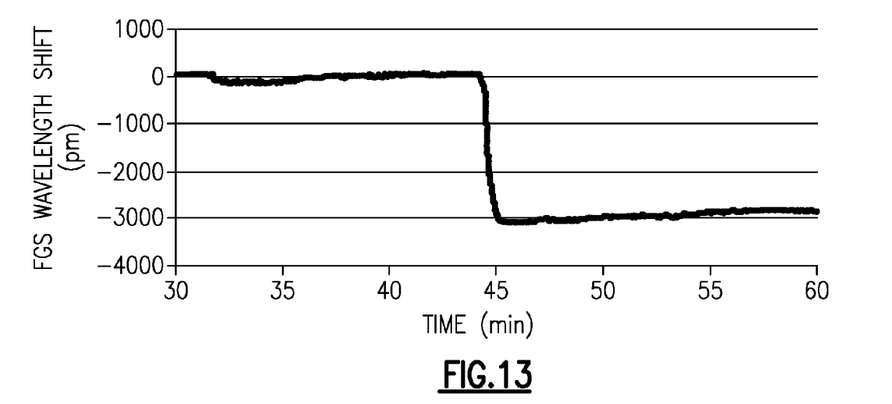
FIG. 13 is a graphical representation of the wavelength shift of the fiber gas sensor of the invention induced by a fuel of about 50% H$_2$ blended with about 50% Natural gas (NG) at room temperature.
Figure 14:
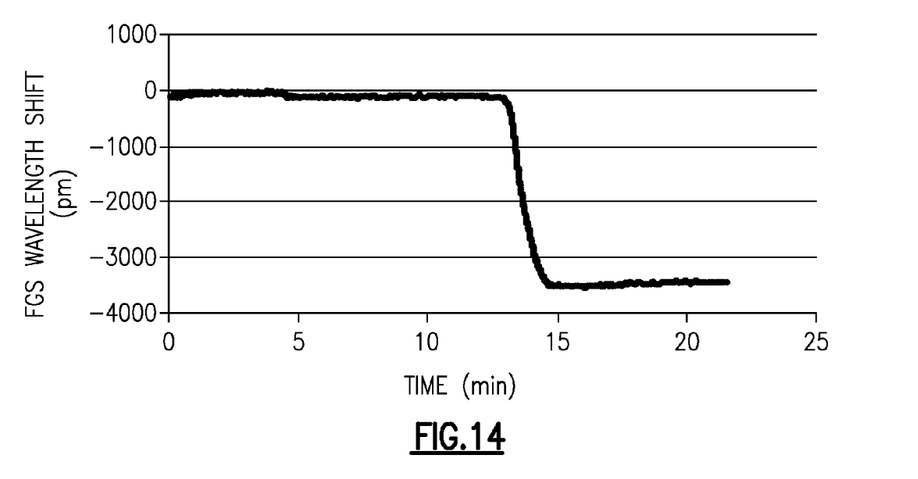
FIG. 14 is a graphical representation of the wavelength shift of the fiber gas sensor of the invention induced by a fuel of about 52% H$_2$ blended with about 48% Natural gas (NG) at room temperature.

In another feasibility study, the sensitivity of the gas sensor 20 from two different gas concentrations in a combustion cell of an operating gas turbine was studied. As shown in FIG. 13, the FGS 20 has a wavelength shift response of about 3000 pm or about 3 nm in fuel in which about 50% $H_2$ was blended with about 50% NG. As shown in FIG. 14, the FGS 20 has a wavelength shift response of about 3500 pm or about 3.5 nm in fuel in which about 52% $H_2$ was blended with about 48% NG. The gas sensor 20 of the invention demonstrated that only a 2% increase in $H_2$ leads to a 500 pm shift in wavelength response. Such an additional 500 pm shift in wavelength response represents a high degree of sensitivity as compared to conventional gas sensor devices. Thus, the effective control of the sensing material morphology of the sensing layer 42 greatly improved the sensitivity of the fiber gas sensor 20.

Figure 15:
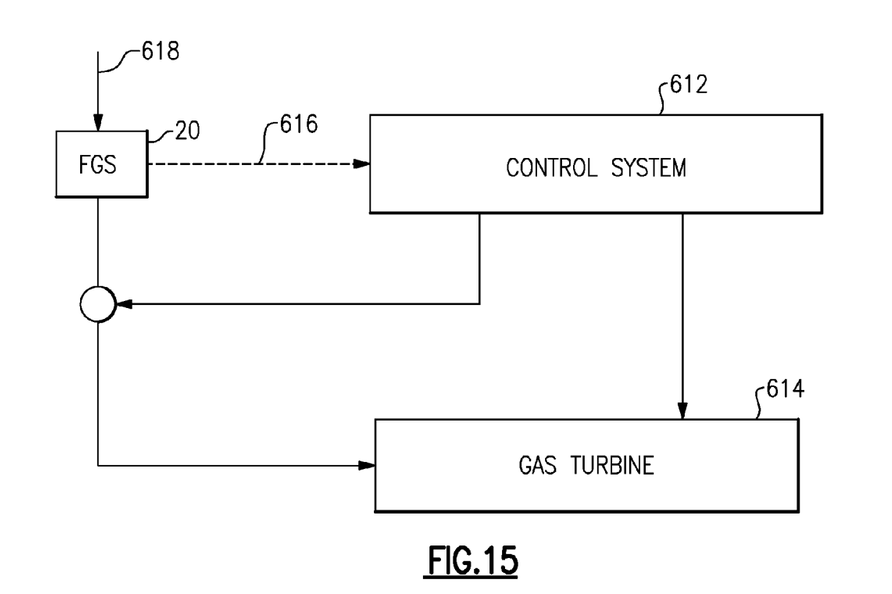
FIG. 15 is a schematic representation of a fuel delivery control system for a gas turbine using the fiber gas sensor of the invention.

In one potential embodiment, the FGS 20 can be integrated into a fuel delivery control system 612 of a gas turbine 614, as shown in FIG. 15. In this embodiment, data output 616 from the FGS 20 is integrated with the control system 612 for the gas turbine 614. The FGS 20 is connected to a fuel supply line 618 to measure the gas composition, for example, the amount of hydrogen (H2) in the gas. In this embodiment, the fuel can be any gas containing hydrogen, which could include syngas (H2+CO) from a gasification plant, a hydrogen/nitrogen gas blend coming from a gasification plant with carbon capture, or hydrogen containing gas from an industrial process. In the case of industrial process gas, the hydrogen could be carried with an inert gas, such as nitrogen (N2), or it could be carried by another reactive gas, such as methane (CH4). The FGS 20 measures the amount of hydrogen in the gas and then sends this data to the gas turbine control system 612. The control system 612 uses this information to determine if the energy content of the fuel gas is within acceptable limits at any given time, or if based on the application of control logic, the energy content of the gas is expected to shift to non-acceptable levels, either above or below an acceptable range. If the energy content is not in the acceptable range, the control system 612 could adjust the fuel flow rate, the air flow rate, or the rate of diluent flow (if any) into the gas turbine combustion system to bring the fuel's energy density into an acceptable range.

As described above, a fiber optic grating-based fiber gas sensor has been invented for industrial systems and applications that need measurements of hydrogen concentration. For example, the sensing device can be used in a coal gasification based power plant that uses hydrogen-rich Syngas or gas turbine power generation plants that use natural gas blended with $H_2$. At the same time, the disclosed sensing technology can be applied to detection of $H_2$ concentrations in gas streams containing H2 in chemical, healthcare, or industrial/petrochemical plants. $H_2$ sensing is very crucial for fuel composition monitoring and control for turbines that use either Syngas or Natural gas (NG) blended with $H_2$ as fuel. For other chemical or petrochemical, $H_2$ sensing enables composition control, which is in turn, is needed for optimal performance of the respective system components such as reactors, distillation columns, blast furnaces, and the like, needing $H_2$ measurement.

While the invention has been described in terms of various specific embodiments, those skilled in the art will recognize that the invention can be practiced with modification within the spirit and scope of the claims.

What is claimed is:

1. A fiber gas sensor, comprising:
   a fiber core having a longitudinal axis;
   a first refractive index periodic modulated grating structure having a first amplitude modulation profile positioned about the fiber core for sensing a localized gas concentration;
   a second refractive index periodic modulated grating structure having a second amplitude modulation profile positioned about the fiber core at a distance along the longitudinal axis with respect to the first refractive index periodic modulated grating structure for sensing a localized temperature;
   a fiber cladding positioned about the first and second refractive index periodic modulated grating structures; and
   a sensing layer positioned about the fiber cladding of the first refractive index periodic modulated grating structure, the sensing layer including a sensing material made of a Pd-based alloy,
   wherein the gas sensor is capable of providing a temperature-corrected determination of the localized gas concentration.

2. A gas sensor according to claim 1, wherein the first refractive index periodic modulated grating structure comprises one of a long-period fiber grating structure and a short-period fiber grating structure.

3. A gas sensor according to claim 1, wherein the amplitude modulation profile of one of the first and second refractive index periodic modulated grating structures has a modulation along the longitudinal axis with a pitch size of about 100 microns to about 600 microns.

4. A gas sensor according to claim 1, wherein the second refractive index periodic modulated grating structure comprises a short-period fiber grating structure.

5. A gas sensor according to claim 4, wherein the short-period fiber grating structure comprises a fiber Bragg grating (FBG) structure.

6. A gas sensor according to claim 1, further comprising an adhesive layer positioned between the fiber cladding and the sensing layer.

7. A gas sensor according to claim 1, wherein one of the first and second refractive index periodic modulated grating structures has one of a uniform profile, a blazed profile, an apodized profile, and a blazed and apodized profile.

8. A gas sensor according to claim 1, wherein the Pd-based alloy is made of a group consisting of nano-PdOx, nano-Pd(x)Au(y)Ni(1-x-y) and nano-Pd/Au/WOx.

9. A gas sensor according to claim 1, wherein the gas sensor is integrated into a fuel delivery control system of a gas turbine.

10. A fiber gas sensor, comprising:
a fiber core having a longitudinal axis;
a first short-period fiber grating structure having a first amplitude modulation profile positioned about the fiber core for sensing a localized gas concentration;
a second short-period fiber grating structure having a second amplitude modulation profile positioned about the fiber core at a distance along the longitudinal axis with respect to the first short-period fiber grating structure for sensing a localized temperature;
a fiber cladding positioned about the first short-period and second short-period fiber grating structures; and
a sensing layer positioned about the fiber cladding of the first short-period fiber grating structure, the sensing layer including a sensing material made of a Pd-based alloy,
wherein the gas sensor is capable of providing a temperature-corrected determination of the localized gas concentration.

11. A gas sensor according to claim 10, wherein the amplitude modulation profile of the first short-period fiber grating structure has a modulation along the longitudinal axis with a pitch size of about 0.5 microns.

12. A gas sensor according to claim 10, wherein the second short-period fiber grating structure comprises a fiber Bragg grating (FBG) structure.

13. A gas sensor according to claim 10, further comprising an adhesive layer positioned between the fiber cladding and the sensing layer.

14. A gas sensor according to claim 10, wherein one of the first short-period fiber grating structure and the second short-period fiber grating structure has one of a uniform profile, a blazed profile, an apodized profile, and a blazed and apodized profile.

15. A gas sensor according to claim 10, wherein the Pd-based alloy is made of a group consisting of nano-PdOx, nano-Pd(x)Au(y)Ni(1-x-y) and nano-Pd/Au/WOx.

16. A sensing system, comprising:
at least one fiber gas sensor as recited in claim 1;
a FC/APC connector operably coupled to each fiber gas sensor; and
one of an optical splitter/combiner and an optical switch operably coupled to the FC/APC connector.

17. A sensing system according to claim 16, wherein the optical splitter/combiner is a 1×2, 1×3, 1×4, and 1×8 type.

18. A sensing system according to claim 16, wherein the optical switch is a 1×16 type.

19. A sensing system according to claim 16, wherein the sensing system comprises one of a reflection-based sensing system and a transmission-based sensing system.

20. A sensing system according to claim 16, wherein the sensing system is operated in one of a constant temperature condition for single composition detection or at a temperature modulated condition for multi-composition detection.

* * * * *